(12) United States Patent
Brahm et al.

(10) Patent No.: US 9,408,650 B2
(45) Date of Patent: Aug. 9, 2016

(54) OSSEOUS TISSUE DELIVERY DEVICE

(71) Applicant: KT, LLC, Germantown, TN (US)

(72) Inventors: Timothy R. Brahm, Germantown, TN (US); Kevin Foley, Germantown, TN (US)

(73) Assignee: KT, LLC, Germantown, TN (US)

( * ) Notice: Subject to any disclaimer, the term of this patent is extended or adjusted under 35 U.S.C. 154(b) by 154 days.

(21) Appl. No.: 14/215,719

(22) Filed: Mar. 17, 2014

(65) Prior Publication Data

US 2014/0276877 A1    Sep. 18, 2014

Related U.S. Application Data

(60) Provisional application No. 61/787,867, filed on Mar. 15, 2013.

(51) Int. Cl.
| | | |
|---|---|---|
| *A61B 17/88* | (2006.01) | |
| *A61L 27/36* | (2006.01) | |
| *B01F 15/02* | (2006.01) | |
| *A61B 17/00* | (2006.01) | |

(52) U.S. Cl.
CPC ......... *A61B 17/8802* (2013.01); *A61B 17/8805* (2013.01); *A61B 17/8822* (2013.01); *A61B 17/8836* (2013.01); *A61L 27/3604* (2013.01); *A61L 27/3608* (2013.01); *B01F 15/0258* (2013.01); *B01F 15/0278* (2013.01); *A61B 2017/0023* (2013.01); *A61B 2017/8838* (2013.01); *A61L 2400/06* (2013.01); *A61L 2430/02* (2013.01); *B01F 2215/0029* (2013.01)

(58) Field of Classification Search
CPC ................... A61B 2017/0023; A61B 17/8802; A61B 17/8805; A61B 17/8822; A61B 17/8836; A61B 2017/8838; A61C 5/04; A61C 5/06; A61C 5/062; A61C 5/068; A61L 27/3604; A61L 27/3608; A61L 2400/06; B01F 2215/0029
See application file for complete search history.

(56) References Cited

U.S. PATENT DOCUMENTS

| | | | | |
|---|---|---|---|---|
| 2006/0164913 | A1* | 7/2006 | Arramon | B01F 3/1228 366/139 |
| 2007/0255200 | A1* | 11/2007 | McLean | A61C 5/068 604/82 |
| 2008/0065088 | A1* | 3/2008 | Hughes | B01F 5/0685 606/93 |

\* cited by examiner

*Primary Examiner* — Larry E Waggle, Jr.
(74) *Attorney, Agent, or Firm* — Brinks Gilson & Lione

(57) ABSTRACT

A mixing and delivery device for osseous tissue is provided. A kit for use by a medical professional is also provided.

7 Claims, 2 Drawing Sheets

OSSEOUS TISSUE DELIVERY DEVICE

CROSS-REFERENCE TO RELATED APPLICATIONS

This application claims priority to U.S. Provisional Patent Application No. 61/787,867 filed Mar. 15, 2013, the contents of which is incorporated herein in its entirety.

FIELD OF THE INVENTION

The present invention is directed to a device for the controlled mixing and delivery of a bone substitute material to a site on or within the human body.

BACKGROUND OF THE INVENTION

Injectable bone substitute materials are used for the repair and augmentation of orthopedic fractures and defects. Bone substitute materials can also be used in certain diagnostic or therapeutic procedures that require the formation of a cavity in a bone mass. Bone substitute materials can be used to treat any bone, for example, bone which due to osteoporosis, avascular necrosis, cancer, or trauma, is fractured or is prone to compression fracture or collapse. These conditions, if not successfully treated, can result in deformities, chronic complications, and an overall adverse impact upon the quality of life.

Various types of devices have been used for delivering bone substitute material. These devices, however, fail to permit proper mixing and extrusion of a bone substitute material. The present device seeks to address these shortcomings

SUMMARY OF THE INVENTION

According to one aspect, a mixing and delivery device for a bone substitute material is provided. The device includes a liquid chamber adapted to receive a liquid composition, a bone substitute material chamber adapted to receive a bone substitute material, optionally, a liquid delivery port located on a proximal end of the liquid chamber, a barrel having a plurality of internal threads, a plunger having a plurality of external threads capable of engaging the internal threads of the barrel, and a suction port located on a distal end of the plunger. The device is adapted to deliver a controlled amount of liquid composition into the bone substitute material chamber to be absorbed by a loaded bone substitute material. According to one embodiment, the liquid composition is a human birth tissue composition. According to one embodiment, the bone substitute material chamber includes a support member having a plurality of steps capable of supporting a pre-packaged bone substitute material. According to one embodiment, the suction port is adapted to receive a source of negative air pressure or vacuum. According to one embodiment, the device is disposable.

According to another aspect, a kit for use by a medical professional is provided. According to one embodiment, the kit includes one or more devices as provided herein. The further includes at least one set of instructions. According to one embodiment, the device is pre-loaded with a bone substitute material.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

As used herein, the term "human birth tissue" includes, but is not limited to, elements of the placental organ such as, for example, the placental globe, umbilical cord, associated membranes (chorionic membrane and amniotic membrane), other gelatins, fluids, cells and extracellular material obtained from a seronegative, healthy human.

As used herein, the term "bone substitute material" refers to any commercially available natural or synthetic osseous tissue utilized in the repair and reconstruction of human bones (e.g., demineralized bone matrix (DBM)).

The present invention is generally directed to an osseous tissue delivery device adapted to mix a liquid composition with a bone tissue substitute material. The present device is particularly suited to mix at least one human birth tissue composition with at least one bone substitute material. The device is further particularly suited to allow a bone substitute material to optimally absorb a human birth tissue material composition thereby producing a single, homogenous mixture that can be delivered to a particular site on or within the human body. The device is further capable of being fully disposable.

Figure 1:
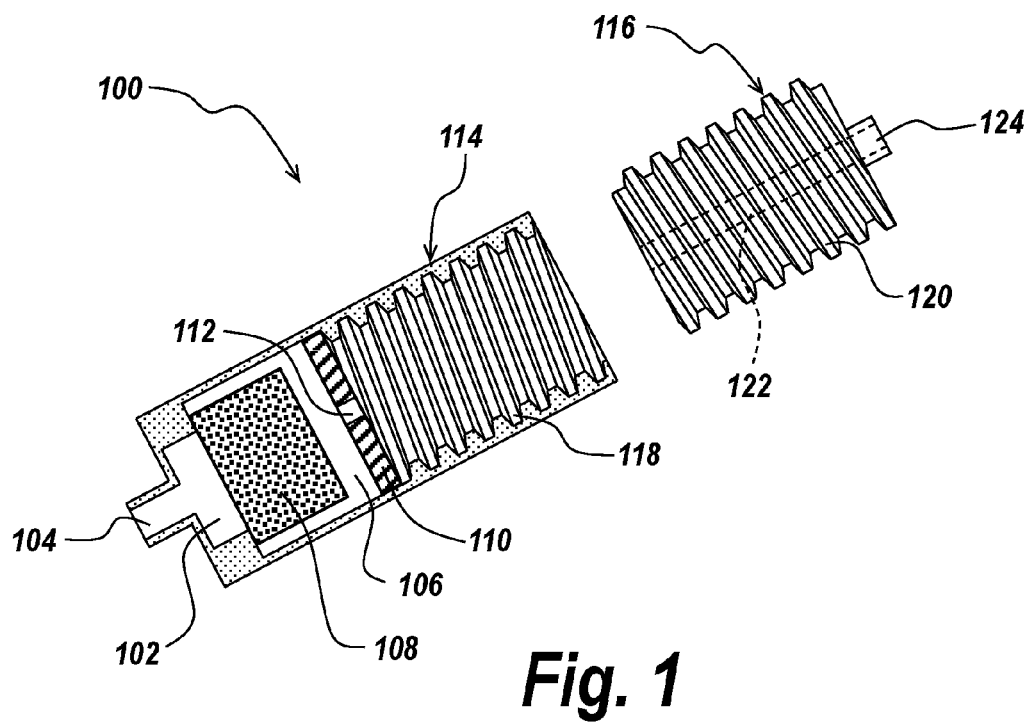
FIG. 1 illustrates a perspective view of a device according to one embodiment.
Figure 4:
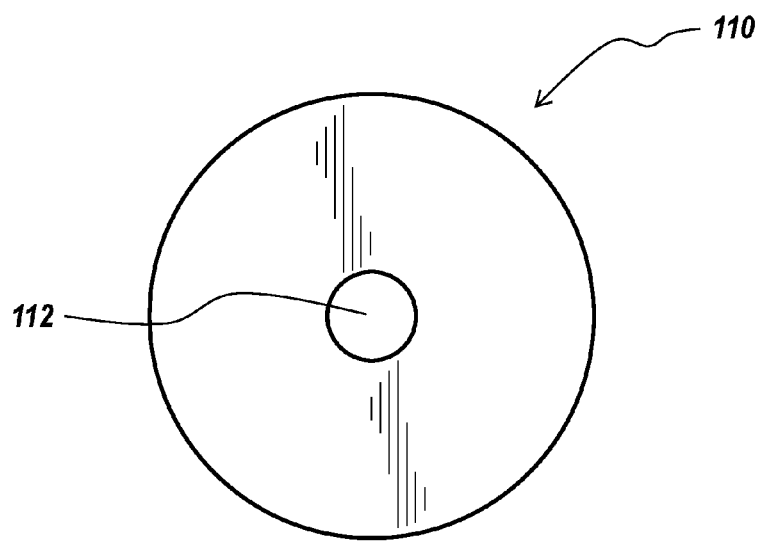
FIG. 4 illustrates a gasket according to one embodiment.

As illustrated in FIG. 1, the device 100 includes a liquid chamber 102 that is in liquid connection with an optional liquid delivery port 104. A bone substitute chamber 106 is adapted to receive a bone substitute material 108. A gasket 110 is located in an upper portion of the bone substitute chamber 106. According to one embodiment, the gasket 110 includes at least one opening 112 (see FIG. 4) to allow for air flow from the bone substitute chamber and into the barrel 114. The barrel 114 includes internal threads 118 adapted to receive (i.e., complimentary to) external threads 120 located a plunger 116. The plunger 116 further includes a central channel or bore 122 that is aligned with the opening 112 of the gasket 110. The plunger 116 further includes a suction port 124 adapted to engage a source of negative air flow. The suction port 122 is substantially aligned with the central bore 118. According to an alternative embodiment, the gasket 110 may be attached to a proximal portion of the plunger 116.

Figure 2:
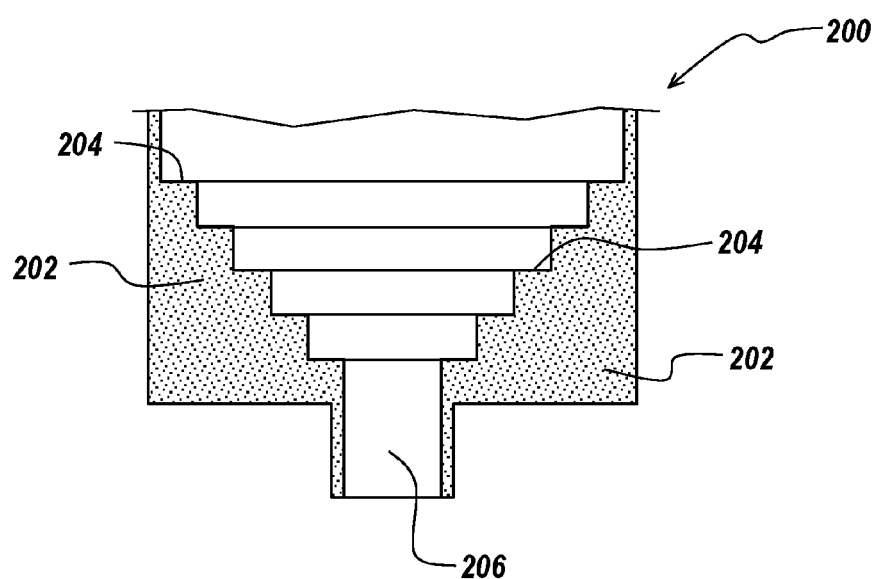
FIG. 2 illustrates a side view of a bone substitute chamber according to one embodiment.

FIG. 2 provides an alternative embodiment of the bone substitute chamber 200. As illustrated, the bone substitute chamber 200 includes support member 202 mounted to an internal surface of the bone substitute chamber 200. The support member 202 includes a plurality of steps 204 adapted to accommodate various sized bone substitute materials.

Thus, the steps 204 allow a bone substitute material to center itself within the bone substitute chamber 200. The bone substitute chamber 200 may further include an optional liquid delivery port 206.

Figure 3:
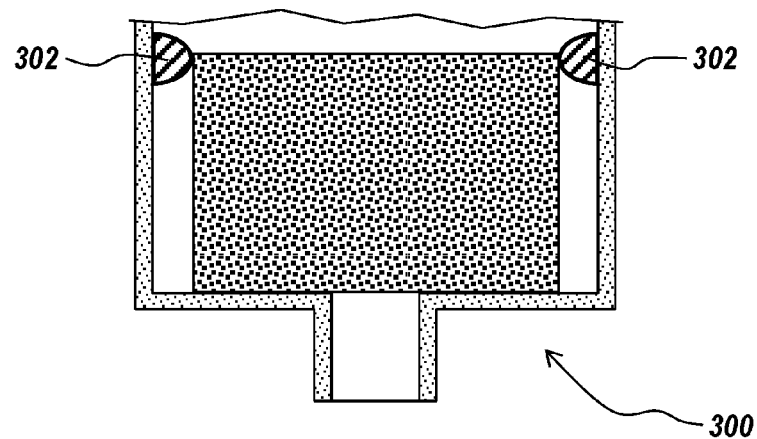
FIG. 3 illustrates a side view of a bone substitute chamber according to one embodiment.

FIG. 3 provides another alternative embodiment of the bone substitute chamber 300. As illustrated, the bone substitute chamber 300 includes at least one seal 302 around an upper perimeter of the chamber 300. The seal 302 is adapted to secure a packed bone substitute material 304 within the chamber 300 prior to mixing.

According to one embodiment, each port (104, 124) includes the male portion of a Luer taper system. The Luer taper system is capable of receiving and securing a medical device having a corresponding female inlet or fitting. According to one embodiment, the Luer taper is a Luer-Lock™ design available from Becton Dickinson. According to another embodiment, the Luer taper system is a Luer-Slip™ design available from Becton Dickinson. Any Luer taper system commonly known in the art, however, may be used.

According to one embodiment, the liquid chamber of the device as described herein is capable of receiving at least one human birth tissue composition. According to one embodiment, the human birth tissue is processed such that the consistency and viscosity of the resulting human birth tissue composition is capable of being loaded and delivered via the device described herein. According to one embodiment, the human birth tissue is subject to moselization and homogenization prior to loading in the device. The human birth tissue composition may further include Minimum Essential Medium, Dulbecco's Modified Eagle's Medium (DMEM), Plasma Lyte-A, human albumin 25% solution, calcium-rich water, dimethyl sulfoxide, alkaline ionized water, and acidic ionized water.

According to one embodiment, the human birth tissue material composition may further include at least one carrier composition. The carrier composition may include Minimum Essential Medium, Dulbecco's Modified Eagle's Medium (DMEM), Plasma Lyte-A, human albumin 25% solution, calcium-rich water, alkaline ionized water, and acidic ionized water. The carrier may further include a variety of optional components to aid in disease resolution, healing, and recovery. Exemplary optional components include, but are not limited to, antibiotics, anti-inflammatory agents, anti-viral agents, growth factors, anti-proliferative agents, cytokines, antihistamines, pain medications, biocides, cellular attractant and scaffolding reagents (e.g., fibronectin), wound healing agents or sealants, nutritional agents (e.g., vitamins), hormones, alkylating agents, immunomodulatory agents (e.g., steroids), collagens, hyaluronic acid, waxes, glycols and derivatives thereof, glyercols and derivatives thereof, oils (including essential oils), fatty acids, cholesterols, alcohols, emollients, adsorbents, lubricants, emulsifying agents, thickening agents, humectants, surfactants, pharmaceutical ingredients, preservatives, antifungal agents, antioxidants, antimicrobial agents, structuring agents, dispersing agents, pH-adjusting components, sequestering or chelating agents, wetting agents, coloring agents, and/or other specialized proteins or small molecules known in the art to be suitable for use in a composition that can be applied onto or within the human body.

In use, the device may be initially loaded with a bone substitute material within the bone substitute chamber. According to one embodiment, the bone substitute material is loaded through the barrel. The bone substitute material may be a pre-packaged, single use bone substitute such as the Bonus™ II demineralized bone matrix product available from Biomet®. The plunger is then engaged or threaded within the barrel. If present, the liquid delivery port may then be immersed in a liquid composition (e.g., human birth tissue material composition or other suitable composition (e.g., saline)). Alternatively, in the absence of a liquid delivery port, the liquid chamber may be manually filled with the liquid composition either prior to or after loading the bone substitute material. The user may then attach or engage a source of negative pressure at the suction port. Once engaged, the negative pressure creates an air flow through the bore thereby drawing liquid composition up through the liquid chamber and into the bone substitute chamber. The negative pressure may be supplied by a vacuum pump or by via a vacuum syringe. By drawing up the liquid composition in this manner, the liquid fully infiltrates the bone substitute material allowing complete and optimal absorption of the liquid within the bone substitute material. In certain embodiments, the negative pressure may be adjusted such that a pre-determined amount of liquid is drawn into the bone substitute chamber and subsequently mixed with the bone substitute material. The resulting homogenous material may be removed by disengaging the plunger from the barrel and physically removing the homogenous bone substitute material. In another embodiment, the homogenous bone substitute material is dispensed back through the liquid delivery port by further advancing the plunger with the barrel. In yet another embodiment, the homogenous bone substitute material may be dispensed by reversing air flow (i.e., applying positive air flow) through the suction port such that the homogenous bone substitute material is forced out through the liquid delivery port.

The resulting homogenous bone substitute material may be in the form of a fine bead, flowable gel, or putty, depending on the amount of liquid drawn. If desired, the homogenous material may then be manipulated or shaped prior to placement on or within an osseous defect (e.g., bone void).

The device as described herein may be used to deliver a bone substitute within a variety of medical applications. In certain embodiments, the device may used in dental applications (e.g., periodontal or maxofacial surgery). In other embodiments, the device may be used in orthopedic applications for sealing, filling and/or otherwise treating bone voids within the body of a patient.

A kit for use by a medical professional is also provided. The kit includes at least one device as described herein. According to another embodiment, the bone substitute chamber may be pre-loaded with an appropriate bone substitute material. In either embodiment, the kit is preserved as per applicable Food and Drug Administration guidelines. The kit further includes at least one set of instructions.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:

1. A mixing and delivery device for a bone substitute material comprising:
   a liquid chamber adapted to receive a liquid composition;
   a bone substitute material chamber adapted to receive a bone substitute material;
   optionally, a liquid delivery port located on a proximal end of the liquid chamber;
   a barrel having a plurality of internal threads;

a plunger having a plurality of external threads capable of engaging the internal threads of the barrel; and a suction port located on a distal end of the plunger, wherein the device is adapted to deliver a controlled amount of liquid composition into the bone substitute material chamber to be absorbed by a loaded bone substitute material.

2. The device of claim 1, wherein the liquid composition is a human birth tissue composition.

3. The device of claim 1, wherein the bone substitute material chamber includes a support member having a plurality of steps capable of supporting a pre-packaged bone substitute material.

4. The device of claim 1, wherein the suction port is adapted to receive a source of negative air pressure or vacuum.

5. The device of claim 1, wherein the device is disposable.

6. A kit for use by a medical professional comprising:

a device according to claim 1.

7. The kit of claim 6, wherein the bone substitute material chamber is pre-loaded with a bone substitute material.

* * * * *